US012589194B2

(12) United States Patent
Whitmore et al.

(10) Patent No.:  US 12,589,194 B2
(45) Date of Patent:      Mar. 31, 2026

(54) APPARATUSES, SYSTEMS, AND METHODS FOR PLASMA RINSEBACK

(71) Applicant: Terumo BCT, Inc., Lakewood, CO (US)

(72) Inventors: Nicole Whitmore, Lakewood, CO (US); Amanda Davison, Lakewood, CO (US); Marlene Bainbridge, Lakewood, CO (US)

(73) Assignee: Terumo BCT, Inc., Lakewood, CO (US)

( * ) Notice:  Subject to any disclaimer, the term of this patent is extended or adjusted under 35 U.S.C. 154(b) by 323 days.

(21) Appl. No.: 18/212,806

(22) Filed:  Jun. 22, 2023

(65)  Prior Publication Data

US 2024/0424182 A1  Dec. 26, 2024

(51) Int. Cl.
*A61M 1/34*  (2006.01)
(52) U.S. Cl.
CPC ................................. *A61M 1/3496* (2013.01)
(58) Field of Classification Search
CPC ........ A61M 1/3496; A61M 2202/0415; A61M 2202/0007; A61M 2202/3646; A61M 2202/3496
See application file for complete search history.

(56)  References Cited

U.S. PATENT DOCUMENTS

| | | | | | |
|---|---|---|---|---|---|
| 5,676,644 | A | * | 10/1997 | Toavs ................. | A61M 1/3641 |
| | | | | | 604/6.11 |
| 2001/0000185 | A1 | * | 4/2001 | Keller ................. | A61M 1/308 |
| | | | | | 604/6.02 |
| 2002/0033370 | A1 | | 3/2002 | Bainbridge et al. | |
| 2009/0166298 | A1 | | 7/2009 | Fender | |
| 2010/0042037 | A1 | | 2/2010 | Felt et al. | |
| 2010/0267538 | A1 | | 10/2010 | Green et al. | |
| 2016/0058938 | A1 | | 3/2016 | Lindner et al. | |

OTHER PUBLICATIONS

International Search Report for corresponding International Patent Application No. PCT/US2024/022816 dated Aug. 2, 2024 (2 Pages).
Written Opinion for corresponding International Patent Application No. PCT/US2024/022816 dated Aug. 2, 2024 (7 Pages).

* cited by examiner

*Primary Examiner* — Jacqueline F Stephens
(74) *Attorney, Agent, or Firm* — Harness, Dickey & Pierce, P.L.C.

(57)  ABSTRACT

A system for minimizing a residual blood value via a plasma rinseback includes a collection bag, a return reservoir, one or more pumps, and one or more lines. The collection bag is configured to store plasma collected from a donor during a donation process. The return reservoir is configured to collect fluid remaining in the system after the donation process is complete. The one or more pumps are configured to be actuated between an operational state and a nonoperational state during the donation process and the plasma rinseback. The one or more lines are configured to couple the collection bag, the return reservoir, the one or more pumps, and the donor. The system is configured to complete the plasma rinseback to return fluid within the system to the donor after the donation process is complete.

20 Claims, 6 Drawing Sheets

— 400

Start

Monitor inlet line — 402

No

Occlusion detected? — 404

Yes

End

— 500

Start

Monitor plasma line — 502

No

Occlusion detected? — 504

Yes

Monitor plasma line — 506

No

Second occlusion detected? — 508

Yes

End

700

702

Processor

Input/Output
Devices

706

704

Memory

APPARATUSES, SYSTEMS, AND METHODS FOR PLASMA RINSEBACK

FIELD

The present disclosure relates to plasma rinseback procedures implemented in apheresis systems.

BACKGROUND

This section provides background information related to the present disclosure which is not necessarily prior art.

Apheresis systems may include rinseback procedures where residual fluid remaining in a disposable kit of the system may be returned to a donor. Typically, not all the fluid remaining in the disposable kit is returned to the donor so there is a residual level that remains in the disposable kit after the return process is completed. Accordingly, it would be desirable to develop assemblies that reduce the residual level remaining in apheresis systems, and also methods of reducing the residual level remaining in apheresis systems.

SUMMARY

This section provides a general summary of the disclosure and is not a comprehensive disclosure of its full scope or all of its features.

The present disclosure provides a system for minimizing a residual blood value via a plasma rinseback includes a collection bag, a return reservoir, one or more pumps, and one or more lines. The collection bag may be configured to store plasma collected from a donor during a donation process. The return reservoir may be configured to collect fluid remaining in the system after the donation process is complete. The one or more pumps may be configured to be actuated between an operational state and a nonoperational state during the donation process and the plasma rinseback. The one or more lines may be configured to couple the collection bag, the return reservoir, the one or more pumps, and the donor. The system may be configured to complete the plasma rinseback to return fluid within the system to the donor after the donation process is complete.

In one or more example embodiments, the plasma rinseback may include a plasma drain state that includes opening a valve of the collection bag, draining the stored plasma from the collection bag for a predetermined amount of time, and closing the valve after the redetermined amount of time. The stored plasma that is drained from the collection bag may be configured to drain into the return reservoir via gravity. In one or more example embodiments, the system is further configured to complete a plasma flush after the plasma rinseback. The plasma flush may include operating a first pump of the one or more pumps to drain the plasma from the return reservoir until a lower sensor of the return reservoir senses air. The plasma may be configured to flow from the return reservoir through the one or more lines to push the collected fluid remaining in the system after the donation process is complete back to the donor. In one or more example embodiments, the residual blood value is an amount of the collected fluid remaining in the system after the plasma flush is complete. The plasma flush may be configured to reduce the amount of the collected fluid remaining in the system after the plasma flush to less than or equal to a threshold value. In one or more example embodiments, the system further includes an alarm that may be configured to actuate if the valve is open for longer than the predetermined amount of time.

In one or more example embodiments, the collection bag may be configured to be located at a threshold distance above the donor.

In one or more example embodiments, the system may additionally monitor the return reservoir after the donation process is complete and operate a first pump of the one or more pumps to drain fluid from the return reservoir if the return reservoir contains more than a threshold amount of fluid. In one or more example embodiments, the system may additionally operate the first pump to return the drained fluid from the return reservoir back to the donor. Operating the first pump to return the drained fluid from the return reservoir back to the donor may additionally include pumping fluid out of a channel of the system. In one or more example embodiments, the system may further include an anticoagulant source. The system may be configured to operate a second pump and a third pump to push anticoagulant from the anticoagulant source through the one or more lines and into the channel after the first pump has pumped fluid out of the channel. In one or more example embodiments, the plasma rinseback may occur after the second pump and the third pump push the anticoagulant through the one or more lines and into the channel.

The present disclosure additionally provides a method for minimizing a residual blood value via a plasma rinseback. The method may include completing a donation process via an apheresis system. The apheresis system may include a collection bag, a return reservoir, one or more pumps, and one or more lines. The collection bag may be configured to store plasma collected from a donor during a donation process. The return reservoir may be configured to collect fluid remaining in the system after the donation process is complete. The one or more pumps may be configured to be actuated between an operational state and a nonoperational state during the donation process and the plasma rinseback. The one or more lines may be configured to couple the collection bag, the return reservoir, the one or more pumps, and the donor. The method may additionally include performing a plasma rinseback to return fluid within the apheresis system to the donor after the donation process is complete.

In one or more example embodiments, performing the plasma rinseback may include opening a valve of the collection bag, draining the stored plasma from the collection bag for a predetermined amount of time, and closing the valve after the redetermined amount of time. The stored plasma that is drained from the collection bag may be configured to drain into the return reservoir via gravity. In one or more example embodiments, the method further includes completing a plasma flush after performing the plasma rinseback. The plasma flush may include operating a first pump of the one or more pumps to drain the plasma from the return reservoir until a lower sensor of the return reservoir senses air. The plasma may be configured to flow from the return reservoir through the one or more lines to push the collected fluid remaining in the system after the donation process is complete back to the donor. In one or more example embodiments, the residual blood value is an amount of the collected fluid remaining in the system after the plasma flush is complete. The plasma flush may be configured to reduce the amount of the collected fluid remaining in the apheresis system after the plasma flush to less than or equal to a threshold value. In one or more example embodiments, the method further includes actuating an alarm if the valve is open for longer than the predetermined amount of time.

In one or more example embodiments, the collection bag may be configured to be located at a threshold distance above the donor.

In one or more example embodiments, the method may further include monitoring the return reservoir after the donation process is complete and operating a first pump of the one or more pumps to drain fluid from the return reservoir if the return reservoir contains more than a threshold amount of fluid. In one or more example embodiments, the method may additionally include operating the first pump to return the drained fluid from the return reservoir back to the donor. Operating the first pump to return the drained fluid from the return reservoir back to the donor may additionally include pumping fluid out of a channel of the system. In one or more example embodiments, the method may further include operating a second pump and a third pump to push anticoagulant from the anticoagulant source through the one or more lines and into the channel after the first pump has pumped fluid out of the channel. In one or more example embodiments, the plasma rinseback may occur after the second pump and the third pump push the anticoagulant through the one or more lines and into the channel.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

Corresponding reference numerals indicate corresponding parts throughout the several views of the drawings.

DETAILED DESCRIPTION

Figure 1:
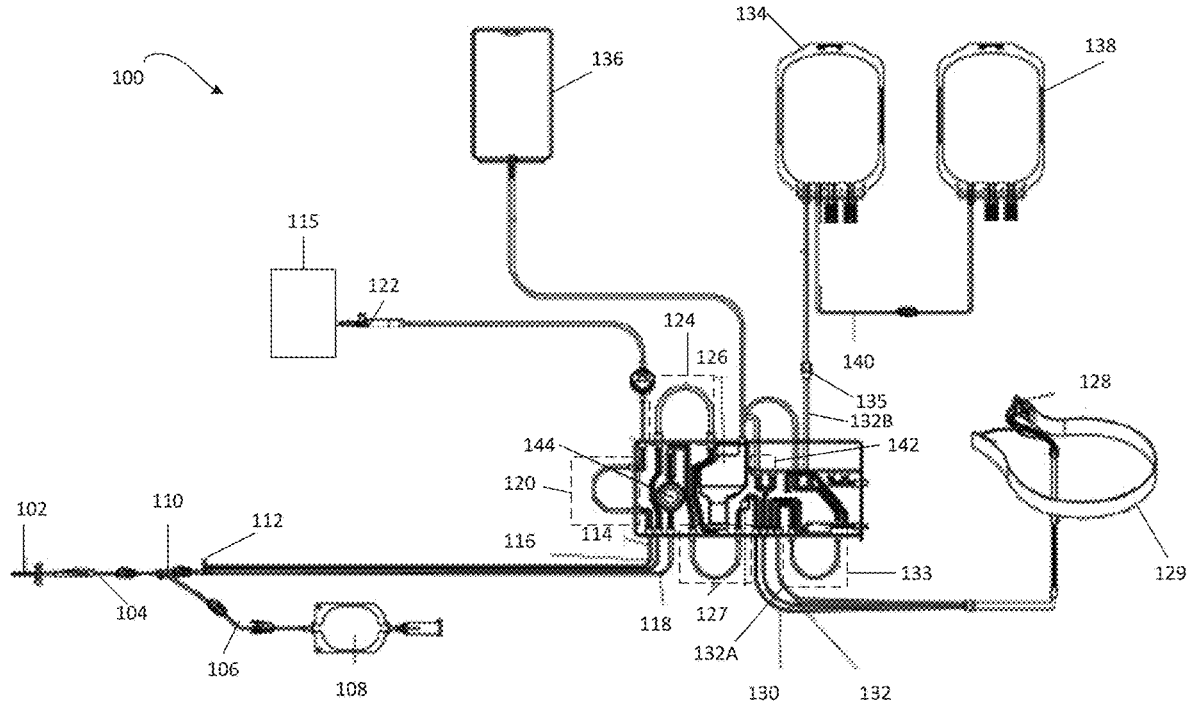
FIG. 1 is a schematic view of an apheresis system according to an example embodiment.

Example embodiments will now be described more fully with reference to the accompanying drawings.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having" are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers, and/or sections, these elements, components, regions, layers, and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The terms memory circuit and memory are a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Example embodiments will now be described more fully with reference to the accompanying drawings.

FIG. 1 shows an apheresis system 100 according to an example embodiment. The apheresis system 100 may be configured to be coupled to a donor in order to collect and/or separate blood components including one or more of plasma and/or red blood cells during a donation process. The apheresis system 100 may include a needle 102 that may be configured to be inserted into a donor, for example, into a vein of a donor via venipuncture. Once the donor is coupled to the apheresis system 100, an intravenous path for blood to flow from the donor to the apheresis system 100 may be formed. The needle 102 may be coupled to a donor line 104 that may provide a path for fluid to flow from the donor into the apheresis system 100.

In one or more example embodiments, the apheresis system 100 may include a sample line 106 configured to connect the donor line 104 to a sample collection bag 108. In one or more example embodiments, the sample line 106 and the donor line 104 may be coupled with a connector 110 that may be a Y connector or another connector configured to stop or allow fluid flow into the sample line 106 and into the sample collection bag 108.

The donor line 104 may be coupled to a manifold 112. The manifold 112 may be configured to provide a connection between the donor line 104 and one or more line of the apheresis system 100. The one or more lines may include a first line 114 that may be an anticoagulant (AC) line, a second line 116 that may be a return line, and a third line 118 that may be a draw line or an inlet line. The first line 114 may be configured to engage with a first pump 120 that may be an AC pump. The first line 114 may additionally be configured to extend to a connector 122 that may be configured to couple the first line 114 to an AC source 115. The AC source 115 may be coupled to the apheresis system 100 to provide AC to the apheresis system 100. The AC may prevent coagulation of blood within the apheresis system 100.

Anticoagulants can include one or more of, but are not limited to, citrate and/or unfractionated heparin. The AC source 115 may be a bag or bottle and bags or bottles described herein can be made from, for example, one or more of, but not limited to: polyvinyl chloride (PVC), plasticized-PVC, polyethylene, ethylene with vinyl acetate (EVA), rubber, silicone, thermoplastics, thermoplastic elastomer, polymers, copolymers, and/or combinations thereof. The volume of AC in the AC source 115 may vary based on the various factors, including the mass of the donor, the volumetric flow of blood from the donor, etc. In one example, the volume in the AC source 115 may be 250 to 500 mL, although the volume in the AC source 115 may be more or less than this volume.

The second line 116 may be configured to engage with a second pump 124 that may be a return pump. The second line 116 may additionally be configured to couple to a return reservoir 126 that may be configured to collect fluids from the apheresis system 100 to be returned to the donor after the donation process is complete. The return reservoir 126 may include a sensor at a first end of the return reservoir. The sensor may be configured to detect air which may provide an indication of a volume of fluid within the return reservoir 126. For example, fluid may be drained from the return reservoir 126 in some example embodiments until the sensor detects air indicating that there is a threshold volume remaining within the return reservoir 126.

The third line 118 may be configured to deliver fluid from the donor line 104 through the apheresis system 100. The third line 118 may be configured to engage with a third pump 127 such as a draw pump or an inlet pump and to deliver fluid from a donor into a centrifuge (not shown) that is configured to separate components of the blood from the donor.

The separated components may be delivered to one or more collection chambers 128 of the apheresis system 100. The one or more collection chambers 128 may be coupled to a channel 129. There may be one or more lines such as a red blood cell line 130 and a plasma line 132 that may be configured to carry red blood cells and plasma to the one or more collection chambers 128 and a plasma bag 134, respectively during the donation process. In one or more embodiments, the plasma bag 134 may be referred to as a collection bag. The plasma bag 134 may be configured to collect plasma obtained from a donor during a donation process via a fourth pump 133 or a plasma pump. The plasma line 132 may include a first portion 132A disposed between the fourth pump 133 and the third pump 127 and a second portion 132B disposed between the plasma bag 134 and the fourth pump 133. In one or more example embodiments, plasma may be released from the plasma bag 134 by opening a plasma valve 135 during a plasma rinseback after the donation process is complete to return fluids within the apheresis system 100 to the donor. The plasma rinseback process will be described in further detail below.

In at least one example embodiment, the first pump 120, the second pump 124, the third pump 127, and/or the fourth pump 133 may be tubing pumps, peristaltic pumps, diaphragm pumps, and/or other pumps configured to manipulate the flow of fluid (e.g., blood, blood components, anticoagulant, saline, etc.) in at least a portion of tubing. For example, the first pump 120, the second pump 124, and/or the third pump 127 may include a motor operatively interconnected with a rotating tubing contact assembly.

In one or more example embodiments, the apheresis system 100 may also include a vent bag 136 and an air removal bag 138. The vent bag 136 may be configured to provide fluid to vent the apheresis system 100. The air removal bag 138 may be configured to collect air from the plasma bag 134 via an air removal line 140 coupled between the plasma bag 134 and the air removal bag 138.

In one or more example embodiments, the apheresis system 100 may also include a red blood cell valve 142. The red blood cell valve 142 may be configured to close and open in response to different operations of the apheresis system 100.

In one or more example embodiment, the apheresis system 100 may also include an access pressure sensor (APS) 144. The APS 144 may be configured to detect occlusion of the third line 118.

FIG. 1 shows how disposable elements of the apheresis system 100 are connected with non-disposable elements illustrated as solid or dashed line boxes. For example, the first pump 120, the second pump 124, the third pump 127, and the fourth pump 133 are illustrated by dashed line boxes to show which of the lines of the apheresis system 100 interact with each of the pumps.

Operation of the various pumps, valves, and blood component separation device, or centrifuge, may be controlled by one or more processors included in the apheresis system 100, and may advantageously comprise a plurality of embedded computer processors that are part of a computer system. The computer system may also include components that allow a user to interface with the computer system, including for example, memory and storage devices (RAM, ROM (e.g., CD-ROM, DVD), magnetic drives, optical drives, flash memory, etc.); communication/networking devices (e.g., wired such as modems/network cards, or wireless such as Wi-Fi); input devices such as keyboard(s), touch screen(s), camera(s), and/or microphone(s); and output device(s) such as display(s), and audio system(s), etc. To assist the operator of the apheresis system 100 with various aspects of its operation, in at least one example embodiment the blood component separation device, or centrifuge, may include a graphical user interface (GUI) with a display that includes an interactive touch screen.

Figure 2:
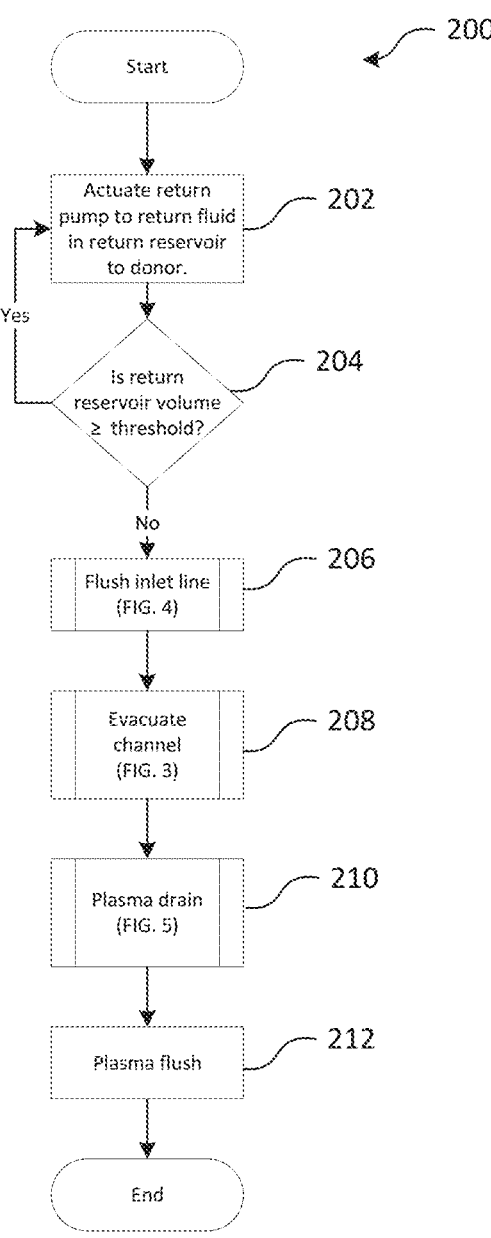
FIG. 2 is a flow chart of plasma rinseback method according to an example embodiment.

FIG. 2 shows a flow chart of a method 200 of performing a plasma rinseback. A plasma rinseback may be a procedure, process, or method of evacuating the apheresis system 100 of fluid to reduce a residual blood value remaining in the apheresis system 100 after a donation process is complete.

In one or more example embodiments, the GUI of the apheresis system 100 may be configured to output a visual indication of an amount of plasma collected from a donor during the plasma rinseback process. The GUI may additionally be configured to output a summary of the plasma rinseback process after the method 200 is complete. The output summary may include an indication of the amount of plasma collected by the apheresis system 100 during a donation process.

The method 200 may start once a donation process is complete and each of the first pump 120, the second pump 124, the third pump 127, and the fourth pump 133 is stopped and each valve within the apheresis system 100 is set to a return state. At step 202, a processor of the apheresis system 100 may actuate the second pump 124 to drain fluid from the return reservoir 126 back to the donor. The second pump 124 may be set to a speed to drain fluid from the return reservoir 126 at a speed between a maximum allowed return flow rate and a maximum needle flow rate allowed for any step of the plasma rinseback process. In some embodiments, the maximum needle flow cate may be about 100 mL/min.

At conditional step 204, a controller of the apheresis system 100 determines whether a volume of fluid in the return reservoir 126 is greater than or equal to a threshold. In at least one example embodiment, the threshold may be a volume of fluid that may be about 10 mL. In other embodiments, the threshold may be a different volume. In at least one example embodiment, the sensor of the return reservoir 126 may be configured to detect whether the volume in the return reservoir 126 is greater than or equal to the threshold. For example, if the sensor does not detect air, then the volume of fluid in the return reservoir 126 may be greater than or equal to the threshold. If the volume is greater than or equal to the threshold, the method 200 may proceed back to the step 202 where the second pump 124 may continue to operate. If the volume is less than the threshold, the method 200 may proceed to step 206.

At the step 206, the processor of the apheresis system 100 may begin a flush inlet process. The flush inlet process may be configured to flush blood remaining in the third line 118 of the apheresis system 100 into the channel 129 via AC. Blood introduced into the channel 129 may be removed by the fourth pump 133 via the plasma line 132. This blood may be collected in the return reservoir 126 as described in further detail herein. In order to complete the flush inlet process, the first pump 120, the third pump 127, and the fourth pump 133 may be actuated. The first pump 120 and the third pump 127 may move AC through the apheresis system 100 to move fluid remaining in the apheresis system 100 back towards the donor. The fourth pump 133 may also be operating during the flush inlet process to evacuate the channel 129 of any fluid. The flush inlet process may be complete when a predetermined volume of fluid is processed by the third line 118. The volume of fluid processed by the third line 118 may be determined by a number of revolutions of one or both of the first pump 120 and the third pump 127. In some embodiments, the predetermined volume of fluid may be about 14 mL of fluid. In other embodiment, the predetermined volume may be smaller or larger than 14 mL.

At step 208, the processor of the apheresis system 100 may begin a channel evacuation process. The channel evacuation process may return fluid within the return reservoir 126 back to the donor while continuing to evacuate the channel 129. The channel evacuation process will be described in detail below with respect to FIG. 3.

At step 210, the processor of the apheresis system 100 may begin a plasma drain process after the channel evacuation process is complete. The plasma drain process may start when the processor opens the plasma valve 135. When the plasma valve 135 is open, plasma from the plasma bag 134 may drain into the return reservoir via gravity. The plasma valve 135 may be open for a predetermined amount of time in order to drain a predetermined amount of plasma out of the plasma bag 134. In some embodiments, the predetermined amount of plasma may be about 30 mL of plasma and the predetermined amount of time may be about nine seconds. In at least one example embodiment, there may be an uncertainty range for the predetermined amount of time before an alarm is raised that the valve 135 has been opened for too long. For example, there may be a two second buffer which may be added to the nine second predetermined amount of time before an alarm condition is triggered within the apheresis system 100.

After the plasma drain process is complete, the processor may perform a plasma flush process at step 212. During the plasma flush process, the processor may operate the second pump 124 to move fluid from the return reservoir 126 through the apheresis system 100 towards the donor until the sensor in the return reservoir 126 senses air. Once the sensor senses air, the level of fluid within the return reservoir 126 is less than a threshold value and the plasma drain process is complete. The second pump 124 may be set to a speed to drain fluid from the return reservoir 126 at a speed between a maximum allowed return flow rate and a maximum needle flow rate allowed for any step of the plasma rinseback process. In some embodiments, the maximum needle flow cate may be about 100 mL/min.

A non-recoverable alarm condition may occur during the plasma drain process if too much fluid is pumped back to the donor. This alarm condition may prevent the drained plasma from reaching the donor during the plasma drain process. In at least one example embodiment, a volume returned to the donor may be monitored after the plasma valve 135 is set to an open position. If the volume of fluid returned to the donor exceeds a threshold value after the plasma valve 135 is opened, an alarm condition may occur. The alarm may be a visual, audible, or other type of alarm that may indicate that this non-recoverable alarm condition has occurred.

In one or more example embodiments, the apheresis system 100 may include additional alarm conditions that are monitored during the plasma drain process. For example, the apheresis system 100 may monitor air within the apheresis system 100 and may prevent air from being returned to the donor. Additionally, the apheresis system 100 may include a power failure mode. The power failure mode may close the plasma valve 135 once power is returned to the apheresis system 100 if the apheresis system 100 loses power during the plasma drain process. If the power failure mode occurs during the plasma drain process, the apheresis system 100 may proceed to donor disconnect once power is returned to the apheresis system. Thus, the method 200 may end early if there is a power failure during the plasma drain process.

The method 200 may end once the plasma drain process is complete. Once the plasma drain process is complete, the donor may be disconnected from the apheresis system 100 and the donation process and the plasma rinseback processes are complete.

Figure 3:
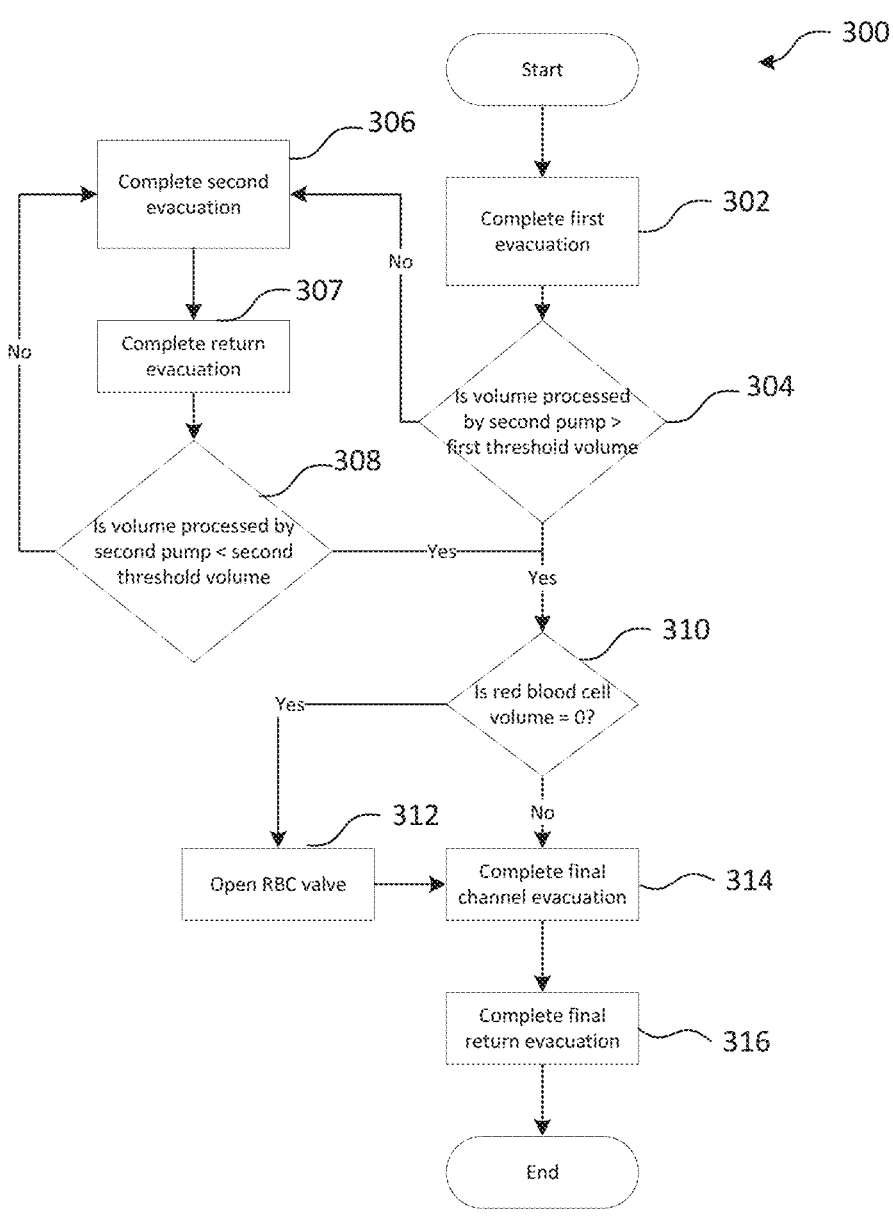
FIG. 3 is a flow chart of an evacuation method of the plasma rinseback method of FIG. 2 according to an example embodiment.

FIG. 3 shows a method 300 of the evacuate channel process of the step 208 of the method 200. The method may start at step 302 with a first evacuation process.

The first evacuation process may include operating the second pump 124 at a first speed. In at least one example embodiment, the first speed may be a minimum speed that may be adjusted for the potential addition of a small volume of AC for whole blood such as Acid Citrate Dextrose Solution A (ACDA) which may mix with the returned whole blood. The fourth pump 133 may be operated at a speed greater than the second pump 124. In at least one example embodiment, the fourth pump 133 may be operated at the first speed. During the first evacuation process, the red blood cell valve 142 may be closed.

After the first evacuation process, the method 300 may proceed to conditional step 304 where the processor determines whether the volume processed by the second pump 124 is greater than a first threshold volume. If the volume processed by the second pump 124 is not greater than a first threshold volume, the method 300 may proceed to step 306 where a second evacuation process is completed. In one or more embodiments, the first threshold volume may be a volume processed through the return reservoir 126. The volume processed by the second pump 124 may be greater than the first threshold volume when the sensor of the return reservoir 126 senses air. When the sensor of the return reservoir 126 detects air, this may indicate that the channel 129 is empty such that fluids are no longer being pulled from the channel 129 into the return reservoir 126. If the sensor of the return reservoir 126 does not detect air, then the second evacuation process may be completed.

The second evacuation process may include operating the fourth pump 133 at the same speed as it was operated in the first evacuation process. The second pump 124 may be turned off for the second evacuation process. The second evacuation process may be complete when a predetermined volume of fluid has been pumped by the fourth pump 133.

After the second evacuation process, the method 300 may proceed to step 307 where a return evacuation process is complete. The return evacuation process may include operating the second pump 124 and the fourth pump 133 at the same speeds as described above for the first evacuation process.

After the return evacuation process, the method 300 may proceed to conditional step 308 where the processor determines whether the volume processed by the second pump 124 is less than a second threshold volume. If the volume processed by the second pump 124 is not less than a first threshold volume, the method 300 may return to the step 306 where the second evacuation process is completed. As described above, the second evacuation process may include operating the fourth pump 133 at the same speed as it was operated in the first evacuation process. The second pump 124 may be turned off during the second evacuation process. If the volume processed by the second pump 124 is less than a first threshold volume, the method 300 may proceed to step 310.

At the step 310, the processor determines whether the red blood cell volume is equal to zero. If the red blood cell volume is equal to zero, the red blood cell valve 142 is opened or set to a return state and the method 300 proceeds to step 314 where a final channel evacuation is completed. If the red blood cell volume is not equal to zero, the method 300 may proceed to the step 314.

The final channel evacuation may include operating the second pump 124 and the fourth pump 133 at the same speeds as described above for the second evacuation process After the final channel evacuation is completed, the method 300 may proceed to step 316 where a final return evacuation is completed. The final return evacuation may include operating the second pump 124 and the fourth pump 133 at the same speeds as described above for the first evacuation process.

In one or more example embodiments, the apheresis system 100 may experience a non-recoverable alarm condition if the apheresis system 100 is unable to evacuate the channel 129. If the channel cannot be evacuated, hypovolemia or air to the donor may occur. The apheresis system 100 may monitor a volume of fluid that is processed by the second pump 124 may indicate that the donor should be disconnected from the apheresis system 100 upon a threshold volume of fluid being processed by the second pump 124. In one or more example embodiments, if hypovolemia is detected, an alarm may be output by the apheresis system. The alarm may be a visual, audible, or other type of alarm that may indicate that this non-recoverable alarm condition has occurred.

Figures 4, 5:
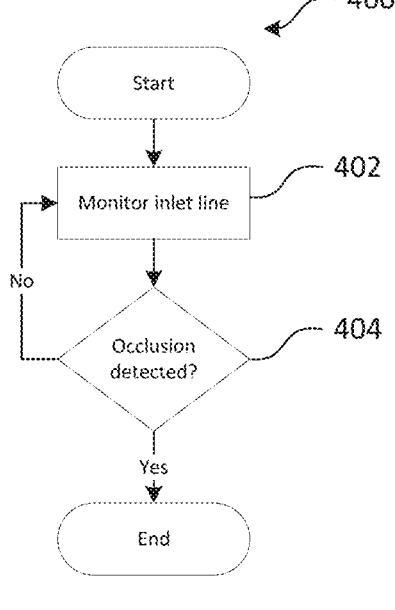
FIG. 4 is a flow chart of a flush inlet process of the plasma rinseback method of FIG. 2 according to an example embodiment.
FIG. 5 is a flow chart of a plasma drain process of the plasma rinseback method of FIG. 2 according to an example embodiment.

FIG. 4 shows a method 400 of monitoring the flush inlet line process of the step 206. The method 400 may start after the return reservoir volume is less than the threshold volume and the flush inlet line process has begun. At step 402, the third line 118 is monitored. At conditional step 404, the processor determines if an occlusion of the third line 118 is detected. If there is no occlusion detected, the method 400 may continue to monitor the third line 118. If there is an occlusion detected, the method 400 may end by halting the plasma rinseback process. Accordingly, if an occlusion is detected at the conditional step 404, the method 200 may end at the step 206. In one or more example embodiments, if an occlusion is detected, an alarm may be output by the apheresis system. The alarm may be a visual, audible, or other type of alarm that may indicate that the method 200 has ended.

The method 400 describes a non-recoverable alarm condition of the apheresis system 100. This alarm condition may result in halting of the method 200 to prevent over infusion of anticoagulant to the donor. In one or more example embodiments, the apheresis system 100 may include the APS sensor 144 that may be configured to detect an occlusion in the third line 118 between the manifold 112 and the APS 144 and an occlusion between the APS 144 and the third pump 127.

In one or more example embodiments, the apheresis system 100 may also be configured to end the method 200 if an occlusion is detected in the first line 114. If an occlusion is detected in the first line 114, there may be less AC pumped through the apheresis system 100 during the method 200 which may result in less fluid being flushed from the apheresis system 100 back to the donor. This may result in elevated residual fluid levels within the apheresis system 100 which is not desirable. Accordingly, if an occlusion is detected in the first line 114, the method 200 may end.

In one or more example embodiments, the apheresis system 100 may also be configured to end the method 200 if the apheresis system 100 is pumping too much AC through the apheresis system 100. If too much AC is being pumped through the apheresis system 100, there is a risk of too much AC reaching the donor. Accordingly, if too much AC is pumped through the apheresis system 100, the method 200 may end.

FIG. 5 shows a method 500 of monitoring the plasma drain process of the step 210. The method 500 may start after the evacuate channel process is complete and the plasma drain process has begun. At step 502, the second portion 132B of the plasma line 132 is monitored. At conditional step 504, the processor determines if an occlusion of the second portion 132B of the plasma line 132 is detected. If there is no occlusion detected, the method 500 may continue to monitor the second portion 132B of the plasma line 132. If there is an occlusion detected, the method 500 may proceed to step 506 to continue monitoring the second portion 132B of the plasma line 132. At conditional step 508, the processor determines if an occlusion of the second portion 132B of the plasma line 132 is detected. If there is no occlusion detected, the method 500 may continue to monitor the second portion 132B of the plasma line 132. If there is an occlusion detected, the method 500 may end by halting the plasma rinseback process. Accordingly, if an occlusion is detected at the conditional step 508, the method 200 may end at the step 210. In one or more example embodiments, if an occlusion is detected, an alarm may be output by the apheresis system. The alarm may be a visual, audible, or other type of alarm that may indicate that the method 200 has ended.

The method 500 describes a non-recoverable alarm condition of the apheresis system 100. This alarm condition may result in halting of the method 200 to prevent over infusion of anticoagulant to the donor. In one or more example embodiments, a message may be displayed on a graphical user interface of the apheresis system 100 if an occlusion is detected at the conditional step 504. A user may be able to manually select a continue option which will allow the method 500 to proceed to the step 506. If a second occlusion is detected at the conditional step 508, the apheresis system 100 may not present an option to a user to continue and may exit the plasma rinseback process, ending the process.

Figure 6:
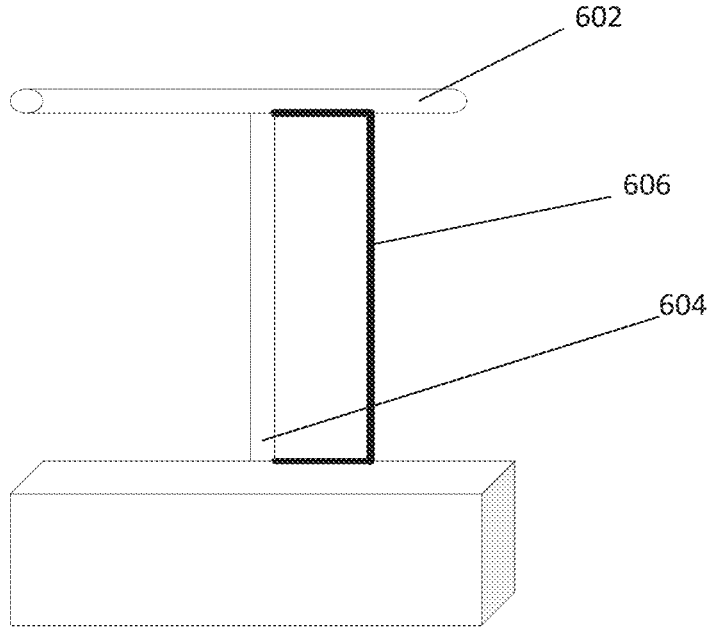
FIG. 6 is a front view of a portion of the apheresis system of FIG. 1 showing a height of a plasma bag according to an example embodiment.

FIG. 6 is a front view of a portion of the apheresis system 100 showing a height of a pole holding the plasma bag 134. The plasma bag 134, not shown in FIG. 6, may be attached to a horizontal pole 602 that may be connected to a vertical pole 604 with a height 606. The height 606 may be configured based on a desired amount of plasma to drain from the plasma bag 134 to flush excess fluid from the apheresis system 100. In at least one example embodiment, the height 606 may be about 18.5 inches. In other embodiments, the height 606 may be greater than 18.5 inches or less than 18.5 inches depending on the amount of residual that may be desired to be flushed out of the apheresis system 100 after completion of the donation process.

Figure 7:
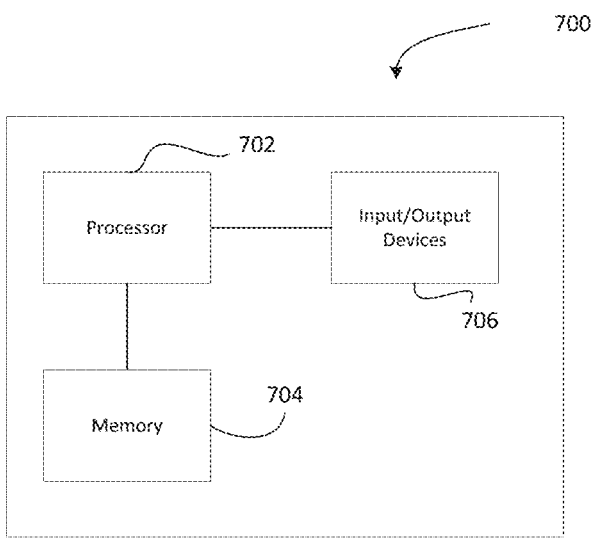
FIG. 7 is a block diagram of a computer system of the apheresis system of FIG. 1 according to an example embodiment.

FIG. 7 is an example embodiment of a computer system 700 that may be included in the apheresis system 100. The computer system 700 may include a processor 702, a memory 704, and one or more input/output devices 706. The processor 702 may be the processor described above with reference to the methods of FIGS. 2-5. As will be appreciated, depending on the implementation of the computer system 700, the computer system 700 may include additional components than those shown in FIG. 7. For example purposes, the example embodiment shown in FIG. 7 will be discussed with regard to the processor 702. However, it should be understood that the computer system 700 may include one or more processors or other processing circuitry, such as one or more Application Specific Integrated Circuits (ASICs).

The memory 704 may be a computer readable storage medium that generally includes a random access memory (RAM), read only memory (ROM), and/or a permanent mass storage device, such as a disk drive. The memory 704 also stores an operating system and any other routines/modules/applications for providing the functionalities of the network node (including UPF, CPF, MPF, etc.) to be executed by the processor 702. These software components may also be loaded from a separate computer readable storage medium into the memory 704 using a drive mechanism (not shown). Such separate computer readable storage medium may include a disc, tape, DVD/CD-ROM drive, memory card, or other like computer readable storage medium (not shown). In some example embodiments, software components may be loaded into the memory 704 via one of the one or more input/output devices 706, rather than via a computer readable storage medium.

The processor 702 or other processing circuitry may be configured to carry out instructions of a computer program by performing the arithmetical, logical, and input/output operations of the system. Instructions may be provided to the processor 702 by the memory 704.

The one or more input/output devices 706 may be wired and may include components that interface the processor 702 with the other input/output components. As will be understood, the one or more input/output devices 706 and programs stored in the memory 704 to set forth the special purpose functionalities of the computer system 700 may vary depending on the implementation of the computer system 700.

The one or more input/output devices 706 may also include one or more user input devices (e.g., a keyboard, a keypad, a mouse, or the like) and user output devices (e.g., a display, a speaker, or the like).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for minimizing a residual blood value via a plasma rinseback, the system comprising:
   a collection bag configured to store plasma collected from a donor during a donation process;
   a return reservoir configured to collect fluid remaining in the system after the donation process is complete;
   one or more pumps configured to be actuated between an operational state and a nonoperational state during the donation process and the plasma rinseback;
   one or more lines configured to couple the collection bag, the return reservoir, the one or more pumps, and the donor, the one or more lines including a plasma line coupling the collection bag to the return reservoir; and
   a plasma valve coupled to the plasma line, the plasma valve enabling fluid to flow, via gravity, from the collection bag, through the plasma line, into the return reservoir when the plasma valve is open,
   wherein the system is configured to complete the plasma rinseback to return fluid within the system to the donor after the donation process is complete.

2. The system of claim 1, wherein the plasma rinseback comprises:
   a plasma drain state that includes
   opening the plasma valve,
draining the stored plasma from the collection bag for a predetermined amount of time, and
   closing the plasma valve after the predetermined amount of time,
   wherein the stored plasma that is drained from the collection bag is configured to drain into the return reservoir via gravity.

3. The system of claim 2, wherein the system is further configured to complete a plasma flush after the plasma rinseback, the plasma flush comprising:
   operating a first pump of the one or more pumps to drain the plasma from the return reservoir until a lower sensor of the return reservoir senses air,
   wherein the plasma is configured to flow from the return reservoir through the one or more lines to push the collected fluid remaining in the system after the donation process is complete back to the donor.

4. The system of claim 3, wherein
the residual blood value is an amount of the collected fluid remaining in the system after the plasma flush is complete; and
   the plasma flush is configured to reduce the amount of the collected fluid remaining in the system after the plasma flush to less than or equal to a threshold value.

5. The system of claim 2, further comprising:
   an alarm configured to actuate if the plasma valve is open for longer than the predetermined amount of time.

6. The system of claim 1, wherein the collection bag is configured to be located at a threshold distance above the donor.

7. The system of claim 1, wherein the system is further configured to
   monitor the return reservoir after the donation process is complete; and operate a first pump of the one or more pumps to drain fluid from the return reservoir if the return reservoir contains more than a threshold amount of fluid.

8. The system of claim 7, wherein the system is further configured to operate the first pump to return the drained fluid from the return reservoir back to the donor, wherein operating the first pump to return the drained fluid from the return reservoir back to the donor additionally includes pumping fluid out of a channel of the system.

9. The system of claim 8, wherein the system further comprises an anticoagulant source; and the system is further configured to operate a second pump and a third pump to push anticoagulant from the anticoagulant source through the one or more lines and into the channel after the first pump has pumped fluid out of the channel.

10. The system of claim 9, wherein the plasma rinseback occurs after the second pump and the third pump push the anticoagulant through the one or more lines and into the channel.

11. A method for minimizing a residual blood value via a plasma rinseback, the method comprising:

completing a donation process via an apheresis system, the apheresis system including a collection bag configured to store plasma collected from a donor during the donation process, a return reservoir configured to collect fluid remaining in the apheresis system after the donation process is complete, one or more pumps configured to be actuated between an operational state and a nonoperational state during the donation process and the plasma rinseback, one or more lines configured to couple the collection bag, the return reservoir, the one or more pumps, and the donor, the one or more lines including a plasma line coupling the collection bag to the return reservoir, and a plasma valve coupled to the plasma line, the plasma valve enabling fluid to flow, via gravity, from the collection bag, through the plasma line, into the return reservoir when the plasma valve is open; and performing the plasma rinseback to return fluid within the apheresis system to the donor after the donation process is complete.

12. The method of claim 11, wherein performing the plasma rinseback comprises:

opening the plasma valve;

draining the stored plasma from the collection bag for a predetermined amount of time; and closing the plasma valve after the predetermined amount of time, wherein the stored plasma that is drained from the collection bag is configured to drain into the return reservoir via gravity.

13. The method of claim 12, wherein the method further includes completing a plasma flush after performing the plasma rinseback, the plasma flush comprising:

operating a first pump of the one or more pumps to drain the plasma from the return reservoir until a lower sensor of the return reservoir senses air, wherein the plasma is configured to flow from the return reservoir through the one or more lines to push the collected fluid remaining in the apheresis system after the donation process is complete back to the donor.

14. The method of claim 13, wherein the residual blood value is an amount of the collected fluid remaining in the apheresis system after the plasma flush is complete; and the plasma flush is configured to reduce the amount of the collected fluid remaining in the apheresis system after the plasma flush to less than or equal to a threshold value.

15. The method of claim 12, further comprising:

actuating an alarm if the plasma valve is open for longer than the predetermined amount of time.

16. The method of claim 11, wherein the collection bag is configured to be located at a threshold distance above the donor.

17. The method of claim 11, wherein the method further comprises:

monitoring the return reservoir after the donation process is complete; and operating a first pump of the one or more pumps to drain fluid from the return reservoir if the return reservoir contains more than a threshold amount of fluid.

18. The method of claim 17, wherein the method further comprises:

operating the first pump to return the drained fluid from the return reservoir back to the donor, wherein operating the first pump to return the drained fluid from the return reservoir back to the donor additionally includes pumping fluid out of a channel of the apheresis system.

19. The method of claim 18, the method further comprises:

operating a second pump and a third pump to push anticoagulant from an anticoagulant source through the one or more lines and into the channel after the first pump has pumped fluid out of the channel.

20. The method of claim 19, performing the plasma rinseback occurs after the second pump and the third pump push the anticoagulant through the one or more lines and into the channel.

* * * * *